United States Patent [19]
Kising

[11] Patent Number: 4,458,534
[45] Date of Patent: Jul. 10, 1984

[54] ULTRASONIC TRANSDUCER PROBE FOR PROVIDING BEAMS WITH ADJUSTABLE ANGLE

[75] Inventor: Jürgen Kising, Cologne, Fed. Rep. of Germany

[73] Assignee: Krautkamer-Branson, Inc., Lewistown, Pa.

[21] Appl. No.: 437,559

[22] Filed: Oct. 29, 1982

[30] Foreign Application Priority Data

Dec. 1, 1981 [DE] Fed. Rep. of Germany ....... 3147482

[51] Int. Cl.³ ............................................ G01N 29/04
[52] U.S. Cl. ........................................ 73/642; 73/644; 73/625
[58] Field of Search ................ 73/642, 644, 625, 626, 73/628; 181/176; 367/150

[56] References Cited

U.S. PATENT DOCUMENTS 3,379,902  4/1968  Harris et al. ........................ 73/642
3,663,842  5/1972  Miller ................................... 73/642
4,340,944  7/1982  Dory ..................................... 73/642

FOREIGN PATENT DOCUMENTS 1285715  8/1972  United Kingdom ................. 73/642

*Primary Examiner*—Howard A. Birmiel
*Attorney, Agent, or Firm*—Ervin B. Steinberg; Philip J. Feig

[57] ABSTRACT

The invention concerns an ultrasonic test probe for use in connection with testing workpieces wherein the angle of propagation of the ultrasonic search beam is adjustable. The probe comprises a linear array of ultrasonic transducer elements and a plastic wedge. An acoustic lens disposed between the array and the wedge causes the individual ultrasonic beams to come to a focus at an acoustic energy exit aperture of the probe. The angle adjustment of the ultrasonic beams is accomplished by energizing in-phase a respective group of transducer elements forming the array.

4 Claims, 5 Drawing Figures

ULTRASONIC TRANSDUCER PROBE FOR PROVIDING BEAMS WITH ADJUSTABLE ANGLE

BRIEF SUMMARY OF THE INVENTION

This invention refers to an ultrasonic transducer probe provided with a plurality of ultrasonic transducer elements and an acoustic lens disposed between the acoustic energy exit aperture of the probe and the transducer elements, and wherein, responsive to energizing selected transducer elements or groups of elements, convergent ultrasonic beams having different angles of propagation are produced and wherein such beams are adapted to be transmitted into a workpiece to be tested via the acoustic aperture of the transducer probe. The present invention, moreover, concerns the use of such a transducer probe for the nondestructive testing of workpieces by means of ultrasonic energy.

Ultrasonic probes of the kind mentioned hereinabove are used in the field of medical ultrasound and are shown, for example, in U.S. Pat. No. 4,183,249 dated Jan. 15, 1980, issued to W. A. Anderson, entitled "Lens System for Acoustical Imaging". The transducer probe described in this patent utilizes an arcuate transducer array in connection with a homocentric lens for providing a relatively small acoustic energy aperture, thus enabling the ultrasonic beams to enter the human body via the intercostal space. The lens causes the ultrasonic beams to come to a focus in a focal plane inside the rib cage.

A similar ultrasonic test probe with arcuately disposed ultrasonic elements is shown also in U.S. Pat. No. 4,204,435 dated May 27, 1980, issued to E. Bridoux et al, entitled "Devices Using Ultrasound for Forming Images" etc. In this embodiment, the lens is not disposed between the sonic energy exit aperture and the transducers, but is located at the exit aperture itself.

The above described test probes are afflicted with a significant disadvantage, namely the requirement to produce an arcuate array of transducer elements and the need for a homocentric acoustic lens.

The present invention discloses an ultrasonic test probe of the above mentioned kind which, despite a small acoustic energy exit aperture, can be produced simply and with relatively low cost. The transducer probe disclosed hereafter is particularly suited as an angle probe for the nondestructive testing of workpieces and includes, moreover, means for providing ultrasonic beams which propagate in the workpiece at selectable angles.

Other advantages and features of the instant invention will be more clearly evident from the following description when taken in conjunction with the accompanying drawings.

DETAILED DESCRIPTION OF THE INVENTION

Figure 1:
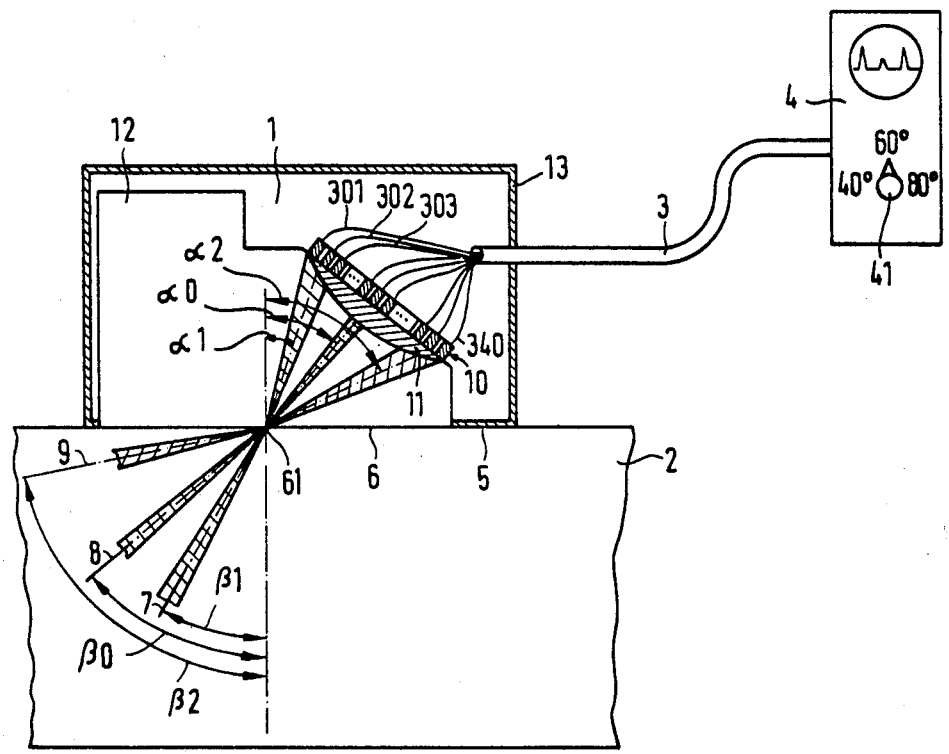
FIG. 1 is a schematic view of the transducer probe disposed upon a workpiece.

Referring now to the figures and FIG. 1 in particular, there is shown a transducer probe 1 disposed on a workpiece 2 which is to be tested for defects, and a cable 3 which connects the transducer probe 1 to an ultrasonic test instrument 4.

The transducer probe 1 comprises essentially a linear array 10 of transducer elements, a lens 11 and a wedge shaped delay line 12. The lens 11 is set into the delay line and is made of material which has a lower acoustic velocity than that of the delay line. Particularly suitable for this purpose has been found silicone as a lens material (c=1 km/sec) and polystyrol (c=2.38 km/sec) for the wedge shaped delay line.

The array 10, lens 11 and the delay line 12 are disposed in a probe housing 13. A multi-conductor cable 3 is fed to the transducer array through an opening in the side of the housing 13. A respective conductor of the cable is connected to one of the transducer elements of the array 10 and to the test instrument 4 which contains the usual pulse circuits for providing an ultrasonic transmit signal to the transducer elements, the required receiver amplifiers and the evaluation circuit, all as known to those skilled in the art.

At the probe surface in contact with the workpiece (underside of the wedge shaped delay line) there is disposed the acoustic aperture 6 through which the acoustic beams exit. This aperture, in the simplest case, is provided by locating the underside of the test probe at this aperture location.

Figure 2:
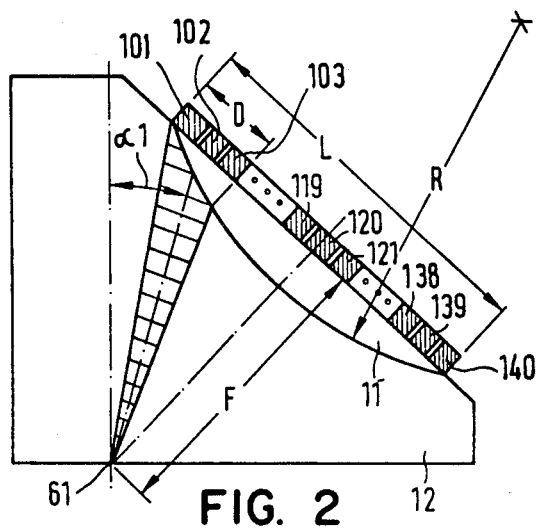
FIG. 2 is a view similar to FIG. 1 having dimensioning symbols.

Explaining now the operation of the transducer probe, FIG. 1 shows three typical ultrasonic beams 7, 8 and 9. In the present embodiment, the beams 7 and 9 are produced by energizing the respective three outer transducer elements, while the beam 8 is produced by energizing the three centrally disposed transducer elements. (In a practical embodiment always eight elements are used instead of the three elements illustrated and described above). If, for example, the three outer elements 101, 102 and 103 are energized simultaneously and in-phase, see FIG. 2, there will be produced a longitudinal wave which has an angle of incidence $\alpha 1$. The quantity of transducer elements, the lens, the curvature as well as the length of the delay line, i.e. the distance between the acoustic energy exit aperture and the transducer array surface, see FIG. 2, are selected to cause the focal line 61 to be disposed at the acoustic energy exit aperture. According to Snell's law:

$$\sin \alpha / \sin \beta = c2/c3$$

shear waves are produced in the workpiece 2 to be tested, which waves approximately have the angle of propagation $\beta 1$, wherein:

c2=acoustic velocity of the longitudinal wave in the polystyrol wedge;
c3=acoustic velocity of the shear wave in the metal medium;
$\alpha$=angle of incidence, and
$\beta$=angle of propagation; also known as angle of refraction or angle of emergence.

Responsive to energizing the centrally located transducer elements 119, 120 and 121 or the outer elements 138, 139 and 140 ultrasonic beams having different angles of incidence ($\alpha 0$, $\alpha 2$) are obtained at the underside of the transducer probe, with the result that ultrasonic beams with respectively different angles of propagation ($\beta 0$, $\beta 2$) are transmitted in the workpiece.

Using the present invention it is possible to provide in the workpiece ultrasonic beams which have different angles of propagation and to receive ultrasonic beams having corresponding angles. It is merely necessary to operate the rotary knob 41, FIG. 1, of the ultrasonic test instrument 4 whereupon a different quantity of juxtaposed transducer elements is connected to the corresponding transmitters. It is possible, of course, to scan a predetermined beam angle range automatically. To this end, initially the elements 101, 102 and 103 are excited, followed by energizing transducer elements 102, 103 and 104, and so forth.

As previously mentioned, the focal line of the ultrasonic beams preferrably is disposed at the acoustic exit aperture 6. This arrangement has the advantage that the required contact surface of the test probe with the workpiece to be tested can be kept relatively small and that the rotational axis falls within the acoustic energy exit surface.

Referring to FIG. 2, the transducer array 10, the lens 11 and the wedge shaped delay line are shown. For example, to provide an angle test probe providing ultrasonic beams having an angle of propagation of 40 to 80 degrees, the angle of incidence must vary between 28 degrees and 47 degrees. The midpoint angle and therefore the wedge angle $\alpha 0$ is 38 degrees. If the distance F between the line 61, defining the beam exit line, and the transducer 10 is chosen to be 45 millimeters, it follows that the required length L of the array is given, being about 50 millimeters. The degree of focusing K, that is the ratio of the near field length of the ultrasonic beam of the energized elements without lens to the near field length with lens must satisfy the condition: $0.7 \leq K < 1$. It has been demonstrated that in this case the divergence of the sound beams in the workpiece to be tested remains relatively small.

Given the distance F, the applicable sound velocity for longitudinal waves c1 and c2 for the silicone lens 11 and the polystyrol wedge 12 and the predetermined aperture D of the simultaneously energized group of transducer elements, it is possible to approximate the radius R of the lens 11 using the formula:

$$R = \frac{F - (c2/c1) \cdot F}{1 - \frac{\lambda}{a^2} F}$$

wherein $a = D/2$ and $\lambda =$ the wavelength of the longitudinal wave in the polystyrol wedge.

It is possible, of course, to preselect the radius of the lens 11 and then determine the aperture D and the quantity of the transducer elements to be energized.

Figure 3:
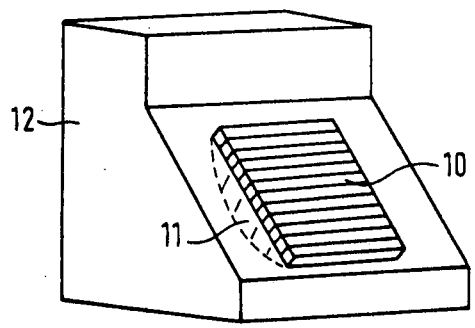
FIG. 3 is a perspective front and side view of the transducer probe.

FIG. 3 depicts a perspective view of the test probe. The array of transducer elements is again identified with numeral 10, the cylindrical lens with numeral 11 and the wedge with numeral 12.

Figure 4:
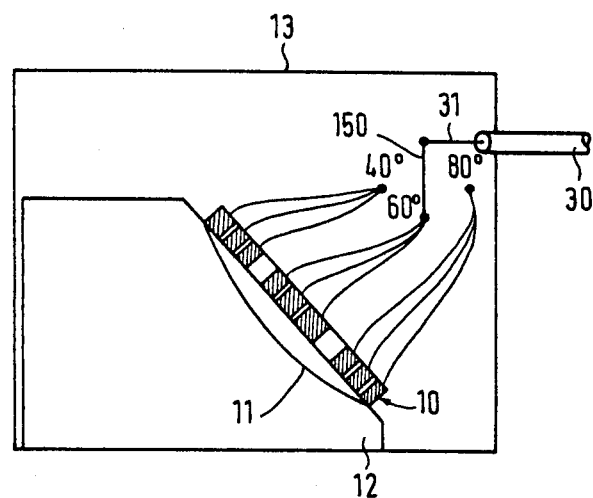
FIG. 4 is a sectional view of the transducer probe illustrating the connection for obtaining three ultrasonic beams with different angles of propagation.
Figure 5:
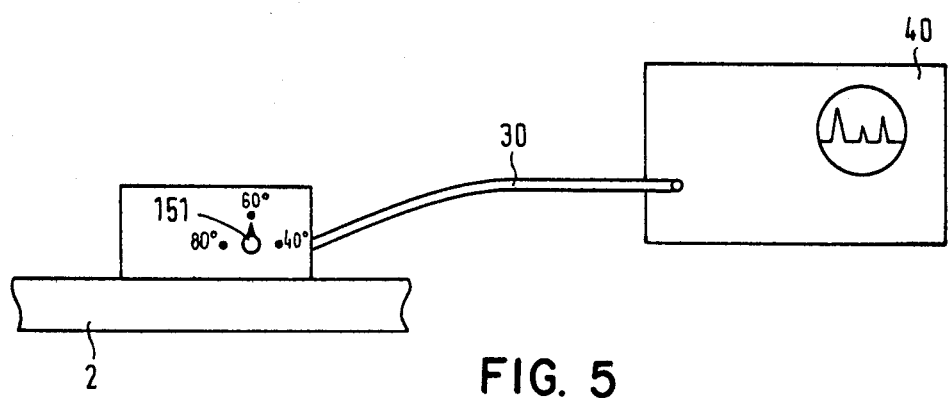
FIG. 5 is a side view of the transducer probe with electrical connection to an ultrasonic test instrument.

As shown in FIG. 1, each transducer element of the transducer array is coupled via a separate conductor 301 to 340 to a respective transmitter and receiver. It is possible, of course, to utilize only a single transmitter and receiver. To this end, as shown for example in FIGS. 4 and 5, a switch 150 with a rotary knob 151 is disposed on the transducer housing 13. The switch serves to select a particular angle for the ultrasonic beam. This latter arrangement has the advantage in that a commercial ultrasonic test instrument 40 can be used. Also, a single conductor cable 30 can be used. Three angles may be selected by the switch and the indicated angles, as is the usual case, refer to angles of propagation utilized for testing a steel workpiece.

What is claimed is:

1. An ultrasonic transducer probe comprising in combination a plurality of transducer elements, a wedge shaped delay line having an acoustic energy exit aperture and an acoustic lens disposed between said transducer elements and the acoustic energy exit aperture of said delay line whereby responsive to energizing selected ones or groups of transducer elements converging ultrasonic beams are produced having different angles of incidence which are transmitted into a workpiece to be tested through said acoustic energy exit aperture the improvement comprising:

said plurality of transducer elements forming a linear array;

said array being inclined relative to the surface of the workpiece to cause only ultrasonic shear waves to be propagated in the workpiece;

the average distance (F) of the array (10) from the acoustic energy exit aperture (6), the curvature of the lens (11) and the acoustic velocity of the lens material and that of the delay line (12) being selected to cause the converging points or converging lines of the individual ultrasonic beams to coincide and be disposed in said acoustic energy exit aperture (6), and the ultrasonic beam produced responsive to energizing the centrally disposed transducer elements being incident in said acoustic energy exit aperture at an angle of substantially 38 degrees, and the length (L) of said linear array being dimensioned to cause in a steel workpiece in contact with said probe ultrasonic beams having an angle of propagation selectable in the range substantially from 40 to 80 degrees.

2. An ultrasonic transducer probe as set forth in claim 1, the degree of focusing K of the group of transducers which are energized simultaneously being in accordance with:

$0.7 \leq K < 1$.

3. An ultrasonic transducer probe as set forth in claim 1, said lens being a cylindrical lens made of silicone and said wedge shaped delay line being made of polystyrol.

4. An ultrasonic transducer probe as set forth in claim 1, and a selector switch coupled to said transducer array to couple said elements to an ultrasonic test instrument for causing selected ones of said elements to be coupled to said instrument for being energized and to provide received ultrasonic signals to said instrument.

* * * * *